(12) United States Patent
Im et al.

(10) Patent No.: US 10,126,243 B2
(45) Date of Patent: Nov. 13, 2018

(54) DEVICE FOR EXAMINING PLANKTON

(71) Applicant: KOREA OCEANIC AND ATMOSPHERIC SYSTEM TECHNOLOGY (KOAST), Seoul (KR)

(72) Inventors: Hyo Hyuc Im, Seoul (KR); Kyu Young Choi, Seoul (KR); Deok Whan Choi, Seoul (KR)

(73) Assignee: KOREA OCEANIC AND ATMOSPHERIC SYSTEM TECHNOLOGY (KOAST), Seoul (KR)

( * ) Notice: Subject to any disclaimer, the term of this patent is extended or adjusted under 35 U.S.C. 154(b) by 0 days.

(21) Appl. No.: 15/028,820

(22) PCT Filed: Jun. 25, 2014

(86) PCT No.: PCT/KR2014/005611
§ 371 (c)(1),
(2) Date: Apr. 12, 2016

(87) PCT Pub. No.: WO2015/056864
PCT Pub. Date: Apr. 23, 2015

(65) Prior Publication Data
US 2016/0258872 A1    Sep. 8, 2016

(30) Foreign Application Priority Data

Oct. 15, 2013 (KR) ........................ 10-2013-0122583

(51) Int. Cl.
*G01N 21/64* (2006.01)
*G01N 33/50* (2006.01)
(Continued)

(52) U.S. Cl.
CPC ..... *G01N 21/6486* (2013.01); *G01N 21/6456* (2013.01); *G01N 33/4833* (2013.01);
(Continued)

(58) Field of Classification Search
CPC . G01N 21/64; G01N 21/6486; G01N 21/6456
(Continued)

(56) References Cited

U.S. PATENT DOCUMENTS

2010/0273208 A1* 10/2010 Takenaka ............... C12M 41/36
435/34
2015/0219548 A1*  8/2015 Nakata .................. C12M 41/36
435/39

FOREIGN PATENT DOCUMENTS

JP     H08261934     10/1996
JP     3166814       3/2011
(Continued)

*Primary Examiner* — David Porta
*Assistant Examiner* — Meenakshi Sahu
(74) *Attorney, Agent, or Firm* — IPLA P.A.; James E. Bame (57) ABSTRACT

A plankton examination apparatus comprises: a sub-pipe in which a transparent pipe unit; a light source unit which radiates only blue-series light; a detection unit which receives light radiated in the direction on the other side outside the transparent pipe unit through the transparent pipe unit from the light source unit and generates an image of the plankton; and a dichroic mirror installed between the transparent pipe unit and the detection unit in such a way as to transmit only red-series light which belongs to the light radiated by the light source unit and passed through the transparent pipe unit and has a wavelength of 620 nm to 780 nm and to deliver the red-series light to the detection unit.

6 Claims, 5 Drawing Sheets

(51) Int. Cl.
G01N 33/53 (2006.01)
G01N 33/483 (2006.01)
(52) U.S. Cl.
CPC ..... *G01N 33/5097* (2013.01); *G01N 33/5308* (2013.01); *G01N 2201/061* (2013.01); *G01N 2201/064* (2013.01)
(58) Field of Classification Search
USPC .............................. 250/461.2; 435/34, 288.7
See application file for complete search history.

(56) References Cited

FOREIGN PATENT DOCUMENTS

| | | |
|---|---|---|
| KR | 1020010032138 | 5/2004 |
| KR | 1020090096400 | 9/2009 |
| WO | WO2006103932 | 10/2006 |

\* cited by examiner

DEVICE FOR EXAMINING PLANKTON

BACKGROUND

The present invention relates to a plankton examination apparatus and, more particularly, to a plankton examination apparatus capable of generating an image of plankton for a sample from a pipeline itself even without obtaining a separate sample and determining the number of individuals of plankton included in the sample.

The present invention relates to a plankton examination apparatus.

The check of the number of individuals of plankton is treated as very important in order to protect a marine ecosystem in other areas due to ballast water in addition to a detailed check and research for an algal bloom or red tide phenomenon.

The check of the number of individuals of plankton is measures for preventing damage to the marine ecosystem attributable to ballast water included in a vessel travelling between countries. This is a precondition for preferentially performing processing on plankton included in ballast water which may threaten the marine ecosystem of another area if a vessel that has departed from a specific area discharges the ballast water in order to lie in another area.

In particular, in order to prevent ecological and economic damage which may be generated by a movement of ballast water and to preserve biological diversity, the International Maritime Organization (IMO) adopted "International Convention for the Control and Management of Ships' Ballast Water and Sediments (BWM)" on February 2004.

Specifically, methods which may be used to process ballast water according to the criteria of the adopted convention may be basically divided into two kinds. The first is an in-line processing method, and the second is an in-tank processing method. The in-line processing method is a method for processing ballast water when the ballast water is introduced and discharged. The in-tank processing method is a method for processing ballast water on the voyage after the ballast water is introduced. Current international ballast water processing technologies include the in-line processing method. In the in-tank processing method, the size of a processing apparatus may be reduced compared with the in-line processing method, but efficiency is practically reconsidered because processing speed needs to be conditioned by taking hours under way into consideration.

In both the methods, the number of individuals of problematic plankton included in ballast water is checked, a corresponding proper processing method is capable of being selected, and a test regarding whether problematic plankton included in discharged ballast water has been processed according to criteria must be performed by performing the final test for ballast water discharged before the processed ballast water is discharged.

However, an expert examination apparatus for checking the number of individuals of plankton included in ballast water has not been provided so far.

Accordingly, in an existing plankton examination apparatus, only a method for photographing a sample and determining, by an expert, determining the number of individuals of problematic plankton included in the sample by determining an image of the photographed sample with the naked eye is performed. Such an existing method has a problem in that it is very difficult to accurately calculate the number of individuals of problematic plankton included in a sample.

A background art of the present invention is disclosed in Korean Patent Application Publication No. 10-1995-7001601, etc., but does not suggest a solution for the aforementioned problems.

SUMMARY OF THE INVENTION

An object of the present invention made to solve the aforementioned problems is to provide a plankton examination apparatus including a light source unit, an optical filter, and a detection unit installed to examine plankton included in a transparent pipe unit formed in a sub-pipe, thereby being capable of checking the number of individuals of plankton included in a sample by detecting a fluorescent characteristic of the plankton included in the sample from a pipeline itself even without obtaining a separate sample.

Furthermore, another object of the present invention is to provide a plankton examination apparatus including an image acquisition unit for detecting a fluorescent characteristic of a sample and generating an image of the sample and an image processing unit for checking the number of individuals of plankton included in the generated image, thereby being capable of checking the accurate number of individuals of plankton included in a sample by checking, by the image processing unit, a plurality of pixels that continuously emits light in an image of the sample displayed on a screen as a single plankton object.

Furthermore, the present invention provides a plankton examination apparatus capable of precisely checking only the number of individuals of actually problematic target plankton and/or active plankton by previously setting conditions of the number of pixels for a plurality of pixels emitting light to form a single object and/or conditions of average brightness or intensity of light of a plurality of pixels emitting light to form a single object.

In accordance with a characteristic of the present invention for achieving the above objects, the present invention includes a sub-pipe in which a transparent pipe unit 50 including a light-transmitting member formed in some section of the sub-pipe and through which a sample including plankton moves; a light source unit 150 which radiates only blue-series light having a wavelength of 380 nm to 480 nm from a direction on one side outside the transparent pipe unit to a direction on the other side of the transparent pipe unit; a detection unit 120 which receives light radiated in the direction on the other side outside the transparent pipe unit through the transparent pipe unit from the light source unit and generates an image of the plankton included in the sample flowing through the transparent pipe unit; and a dichroic mirror 112 installed between the transparent pipe unit and the detection unit in such a way as to transmit only red-series light which belongs to the light radiated by the light source unit and passed through the transparent pipe unit and has a wavelength of 620 nm to 780 nm and to deliver the red-series light to the detection unit.

Furthermore, in accordance with another characteristic of the present invention for achieving the above objects, the present invention includes a sub-pipe in which a transparent pipe unit 50 including a light-transmitting member formed in some section of the sub-pipe and through which a sample including plankton moves; a light source unit 150 which radiates light from a direction on one side outside the transparent pipe unit to a direction on the other side of the transparent pipe unit; a detection unit 120 which receives light radiated in the direction on the other side outside the transparent pipe unit through the transparent pipe unit from the light source unit and generates an image of the plankton included in the sample flowing through the transparent pipe unit; an excitation filter 111 installed between the light source unit and the transparent pipe unit in such a way as to transmit only blue-series light belonging to the light radiated by the light source unit 150 and having a wavelength of 380 nm to 480 nm and to deliver the blue-series light to the transparent pipe unit; and a dichroic mirror 112 installed between the transparent pipe unit and the detection unit in such a way as to transmit only red-series light which belongs to the light radiated by the light source unit and passed through the transparent pipe unit through the excitation filter and has a wavelength of 620 nm to 780 nm and to deliver the red-series light to the detection unit.

In this case, a first light induction member which prevents interference with external light and allows the light radiated by the light source unit to be delivered to the transparent pipe unit through the excitation filter without interference is coupled between the light source unit and the transparent pipe unit. A second light induction member which prevents interference with external light, penetrates the transparent pipe unit, and allows light reflected by the plankton included in the sample to be focused on the detection unit is coupled between the transparent pipe unit and the detection unit.

Furthermore, the detection unit 120 includes an image acquisition unit 121 which detects light reflected by the plankton included in the sample, generates the image of the plankton included in the sample, and displays the generated image on a screen; and an image processing unit 122 which analyzes each of pixels included in the screen on which the generated image is displayed and determines the number of plankton included in the sample, wherein the image processing unit 122 determines a plurality of pixels belonging to the pixels included in the screen and continuously emitting light to be a single object, calculates a total number of objects included in the screen, and determines the total number of objects to be a total number of target plankton included in the screen.

Furthermore, the image processing unit 122 determines only a corresponding object belonging to the objects and having the number of a plurality of pixels continuously emitting light within a range of a predetermined number to be the target plankton and determines the total number of target plankton included in the screen by calculates the total number of target plankton included in the screen.

Furthermore, the image processing unit 122 excludes an object of the objects determined to be the target plankton from the target plankton if an average brightness or intensity value of light of all of pixels forming a single object is out of a predetermined brightness to intensity range of light.

In accordance with the present invention, such as that described above, there can be provided the plankton examination apparatus capable of checking the number of individuals of plankton included in a sample by detecting a fluorescent characteristic of the plankton included in the sample from a pipeline itself even without obtaining a separate sample.

Furthermore, in accordance with the present invention, there can be provided the plankton examination apparatus capable of checking the accurate number of individuals of plankton included in a sample by determining a plurality of pixels continuously emitting light in an image of the sample displayed on a screen to be a single plankton object through the image processing unit.

Furthermore, there can be provided the plankton examination apparatus capable of precisely checking only the number of individuals of actually problematic target plankton and/or active plankton by previously setting conditions of the number of pixels for a plurality of pixels emitting light to form a single object and/or conditions of average brightness or intensity of light of a plurality of pixels emitting light to form a single object.

DESCRIPTION OF REFERENCE NUMERALS

100: plankton examination apparatus according to the present invention
110: optical filter unit 111: excitation filter
112: optical filter 120: detection unit
121: image acquisition unit 122: image processing unit
130: light induction member 141, 142, 143: support member
148: communication unit 149: display unit
150: light source unit

DESCRIPTION OF THE PREFERRED EMBODIMENTS

The merits and characteristics of the present invention and a method for achieving the merits and characteristics will become more apparent from embodiments described in detail in conjunction with the accompanying drawings.

However, the present invention is not limited to the disclosed embodiments, but may be implemented in various different ways. The embodiments are provided to only complete the disclosure of the present invention and to allow those skilled in the art to understand the category of the present invention. The present invention is defined by the category of the claims. The same reference numbers will be used to refer to the same or similar elements throughout the drawings.

A plankton examination apparatus according to an embodiment of the present invention is described below with reference to the drawings.

Figure 1:
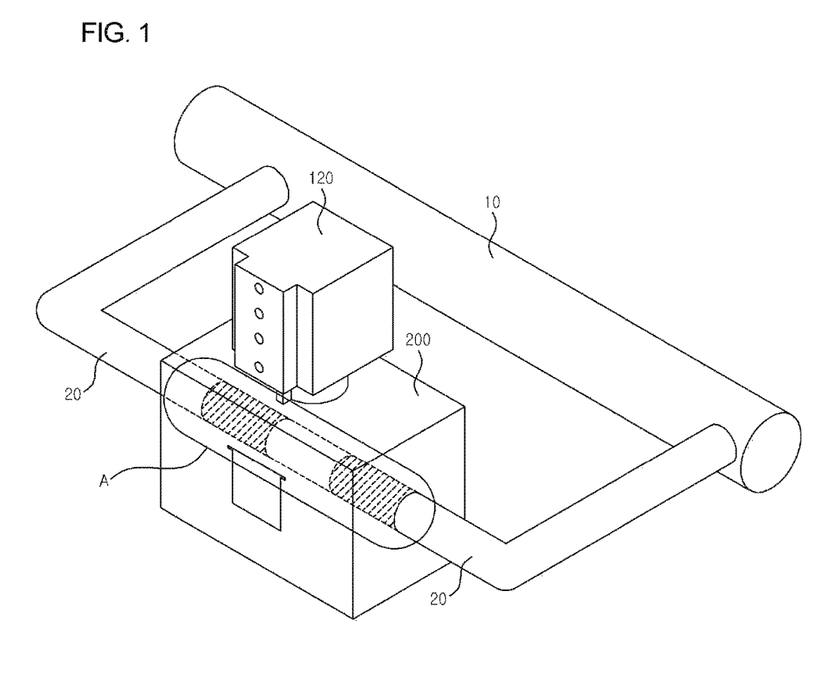
FIG. 1 is a perspective view for illustrating an overall configuration of a plankton examination apparatus according to the present invention.
Figure 2:
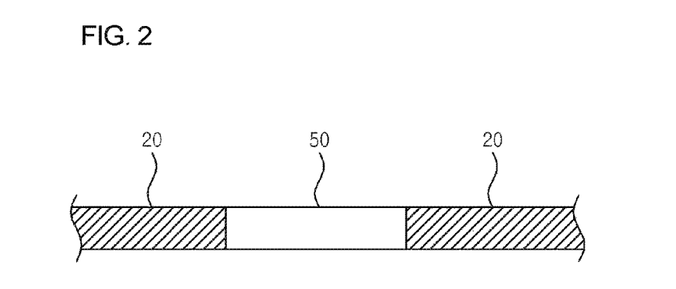
FIG. 2 is a front view showing the construction of a sub-pipe in which a transparent pipe unit has been formed.
Figure 3:
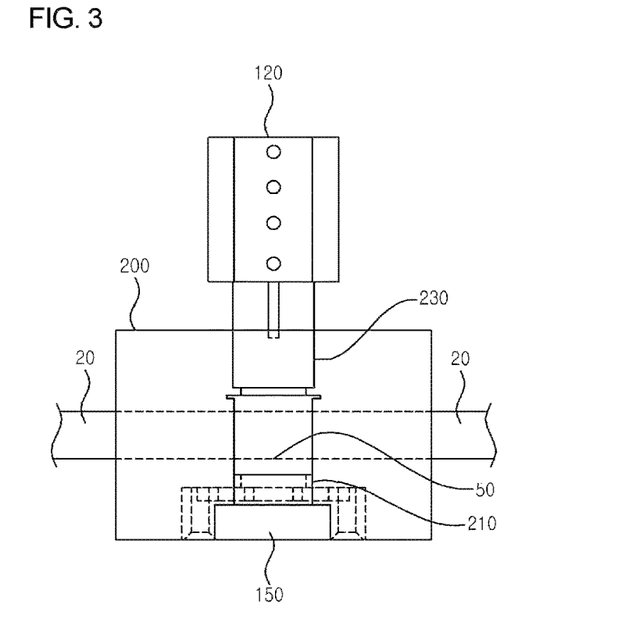
FIG. 3 is a front view showing the construction of the plankton examination apparatus according to the present invention.
Figure 4:
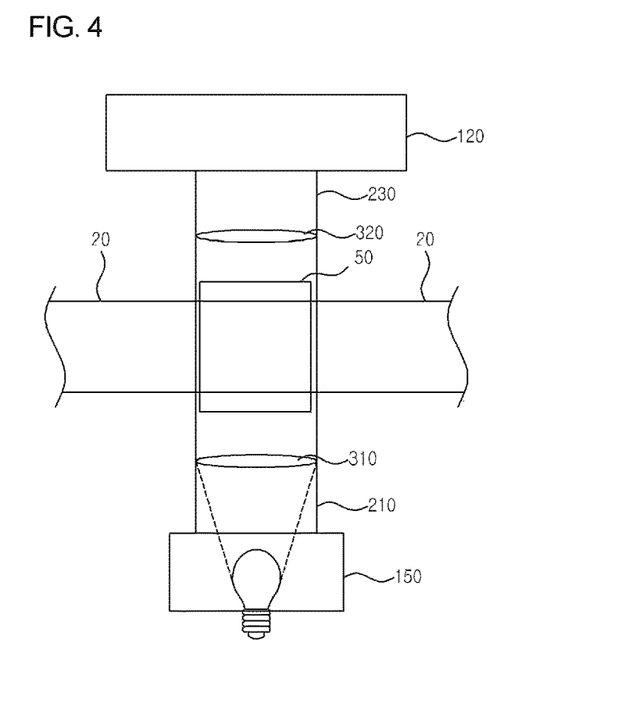
FIG. 4 is a front cross-sectional view of the plankton examination apparatus according to the present invention.
Figure 5:
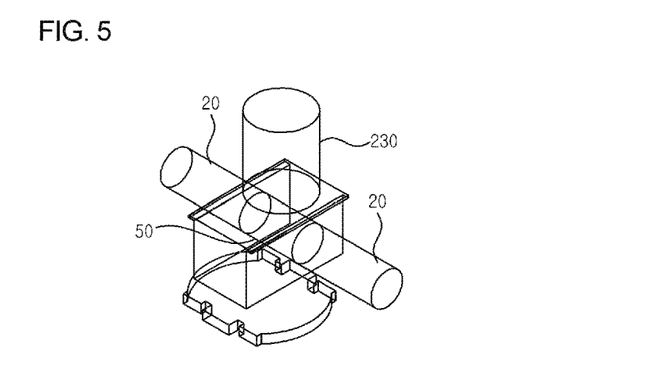
FIG. 5 is a perspective view for illustrating the plankton examination apparatus according to the present invention.
Figure 6:
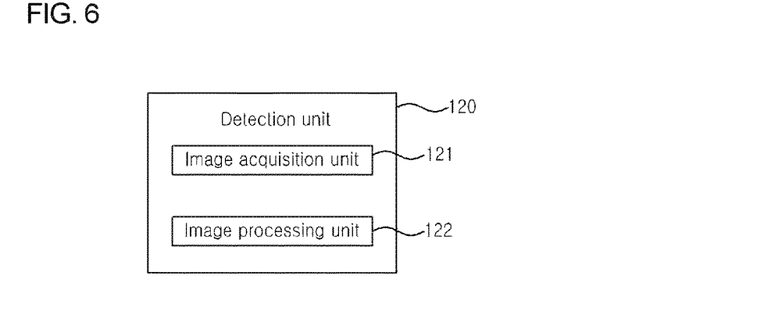
FIG. 6 is a block diagram of a detection unit.

FIG. 1 is a perspective view for illustrating an overall configuration of a plankton examination apparatus according to the present invention. FIG. 2 is a front view showing the construction of a sub-pipe in which a transparent pipe unit has been formed. FIG. 3 is a front view showing the construction of the plankton examination apparatus according to the present invention. FIG. 4 is a front cross-sectional view of the plankton examination apparatus according to the present invention. FIG. 5 is a perspective view for illustrating the plankton examination apparatus according to the present invention. FIG. 6 is a block diagram of a detection unit.

Figure 7:
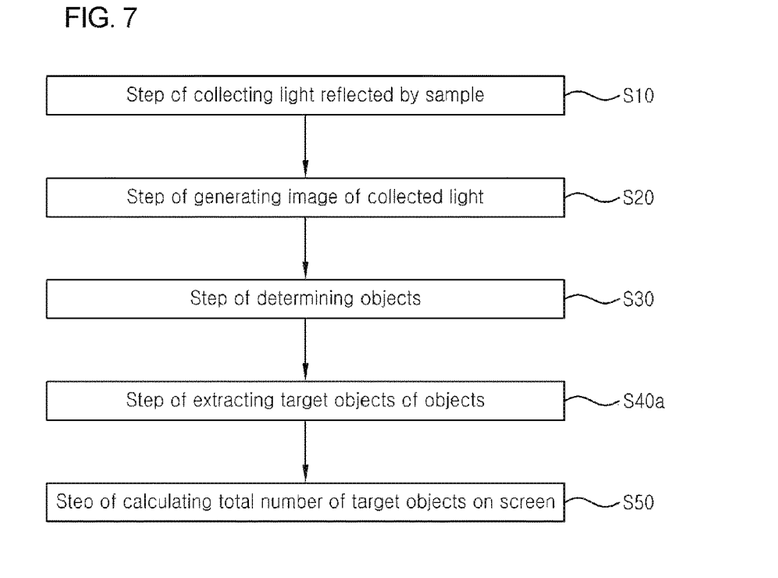
FIG. 7 is a flowchart of a method for determining objects from an image of a sample, preferentially extracting target plankton having a specific size from the determined objects, and calculating a target body, that is, a total number of final target plankton.
Figure 8:
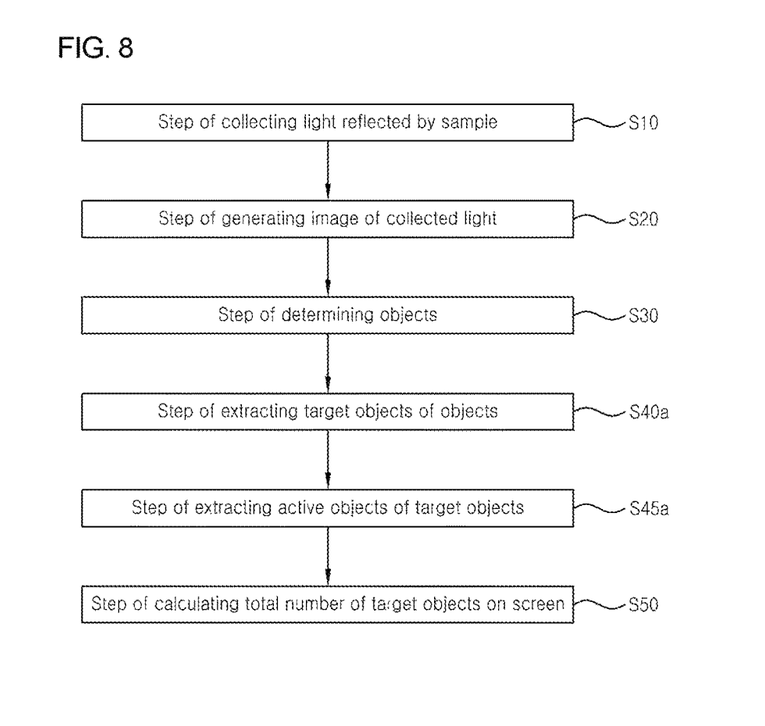
FIG. 8 is a flowchart illustrating that an additional filtering process for active plankton has been added to FIG. 5.
Figure 9:
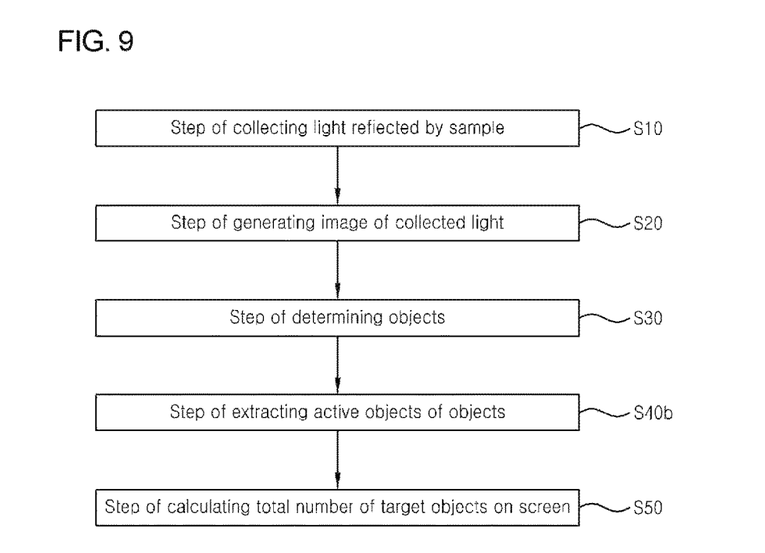
FIG. 9 is a flowchart of a method for determining objects from an image of a sample, preferentially extracting active plankton from the determined objects, and calculating a target body, that is, a total number of final target plankton.
Figure 10:
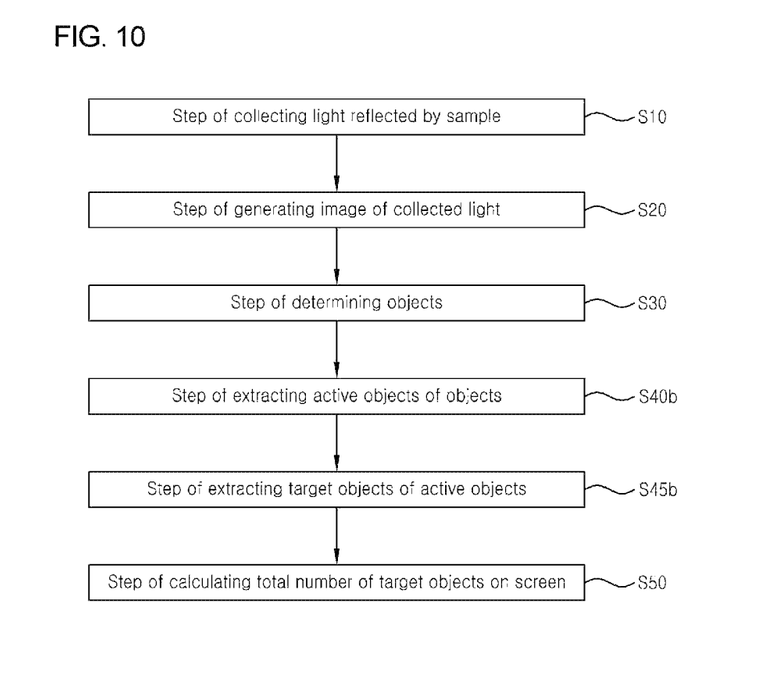
FIG. 10 is a flowchart illustrating that an additional filtering process for target plankton having a specific size has been added to FIG. 7.

Furthermore, FIG. 7 is a flowchart of a method for determining objects from an image of a sample, preferentially extracting target plankton having a specific size from the determined objects, and calculating a target body, that is, a total number of final target plankton. FIG. 8 is a flowchart illustrating that an additional filtering process for active plankton has been added to FIG. 5. FIG. 9 is a flowchart of a method for determining objects from an image of a sample, preferentially extracting active plankton from the determined objects, and calculating a target body, that is, a total number of final target plankton. FIG. 10 is a flowchart illustrating that an additional filtering process for target plankton having a specific size has been added to FIG. 7.

The plankton examination apparatus according to the present invention is an examination apparatus for plankton included in a sample, such as ballast water or a variety of types of seawater and in particular, is a technology very suitable for the examination of plankton for ballast water.

The plankton examination apparatus according to a preferred embodiment of the present invention includes a sub-pipe 20 in which a transparent pipe unit 50 formed of a light-transmitting member is formed in some section of the sub-pipe and through which a sample including plankton moves, a light source unit 150 which radiates light from a direction on one side outside the transparent pipe unit 50 to a direction on the other side of the transparent pipe unit 50, a detection unit 120 which receives light radiated from the light source unit 150 to the direction on the other side outside the transparent pipe unit through the transparent pipe unit 50 and generates an image of the plankton included in the sample flowing through the transparent pipe unit 50, and an optical filter 112 installed between the transparent pipe unit and the detection unit in such a way as to transmit only red-series light that belongs to the light radiated by the light source unit and passed through the transparent pipe unit and that has a wavelength of 620 nm to 780 nm and to deliver only the red-series light to the detection unit.

That is, the plankton examination apparatus according to the present invention is an apparatus in which the transparent pipe unit 50 of a light-transmitting material is formed in some section of a pipe through which ballast water or seawater moves and which radiates light to the transparent pipe unit 50 and determines the number of individuals of plankton included in a sample by detecting an image of plankton included in ballast water or seawater, that is, the sample passing through the transparent pipe unit 50.

In this case, if the light source unit 150 radiates only blue-series light having a wavelength of 380 nm to 480 nm, an excitation filter 111 to be described later is exclude between the light source unit 150 and the transparent pipe unit 50. If the light source unit 150 radiates light to the entire visible ray region, the excitation filter 111 for transmitting only blue-series light that belongs to the light radiated by the light source unit 150 and has a wavelength of 380 nm to 480 nm and for delivering only the blue-series light to the transparent pipe unit 50 will be installed between the light source unit 150 and the transparent pipe unit 50.

That is, if the light source unit 150 radiates only light having a wavelength of 380 nm to 780 nm, the plankton examination apparatus according to the present invention is configured to include the sub-pipe in which the transparent pipe unit 50 formed of a light-transmitting member is formed in some section of the sub-pipe and through which a sample including plankton moves, the light source unit 150 which radiates only blue-series light having a wavelength of 380 nm to 480 nm from the direction on one side outside the transparent pipe unit to the direction on the other side of the transparent pipe unit, the detection unit 120 which receives light radiated from the light source unit to the direction on the other side outside the transparent pipe unit through the transparent pipe unit and generates an image of the plankton included in the sample flowing through the transparent pipe unit, and a dichroic mirror 112 installed between the transparent pipe unit and the detection unit in such a way as to transmit only red-series light that belongs to the light radiated by the light source unit and passed through the transparent pipe unit and that has a wavelength of 620 nm to 780 nm is transmitted and to deliver only the red-series light to the detection unit.

Furthermore, if the light source unit 150 radiates light of the entire visible ray region having a wavelength of 380 nm to 780 nm, the plankton examination apparatus according to the present invention is configured to include the sub-pipe in which the transparent pipe unit 50 formed of a light-transmitting member is formed in some section of the sub-pipe and through which a sample including plankton moves, the light source unit 150 which radiates light from the direction on one side outside the transparent pipe unit to the direction on the other side of the transparent pipe unit, the detection unit 120 which receives light radiated from the light source unit to the direction on the other side outside the transparent pipe unit through the transparent pipe unit and generates an image of the plankton included in the sample flowing through the transparent pipe unit, the excitation filter 111 installed between the light source unit and the transparent pipe unit in such a way as to transmit only blue-series light that belongs to the light radiated by the light source unit 150 and that has a wavelength of 380 nm to 480 nm and to deliver only the blue-series light to the transparent pipe unit, and the dichroic mirror 112 installed between the transparent pipe unit and the detection unit in such a way as to transmit only red-series light that belongs to the light radiated by the light source unit and passed through the transparent pipe unit through the excitation filter and that has a wavelength of 620 nm to 780 nm and to deliver only the red-series light to the detection unit.

That is, the plankton examination apparatus according to the present invention may be configured in two types in which the excitation filter 111 is included or excluded depending on the case where the light source unit 150 radiates only the light of the wavelength of 380 nm to 480 nm and the case where the light source unit 150 radiates the light having the wavelength of 380 nm to 780 nm. A description of other configurations may be the same as that of the above configurations regardless of light radiated by the light source unit 150 and is as follows.

The plankton examination apparatus according to the present invention includes the sub-pipe 50, the light source unit 150, the detection unit 120, and the optical filter 112.

The sub-pipe 50 may be formed of a manifold branched from a main pipe 10 through which ballast water or seawater actually moves.

The light source unit 150 is means functioning as a light source used in an optical microscope, etc. and may include a light source which emits light having the lowest 380 nm, that is, the wavelength region of a common visible ray, to a wavelength having a range of the highest 780 nm or emits only light having a wavelength of 380 nm to 480 nm. A description of the light source unit 150 has been described above.

That is, if the light source unit 150 includes a light source for radiating only the blue-series light having the wavelength of 380 nm to 480 nm, the element of the excitation filter 111 to be described later is excluded.

That is, if the light source unit 150 radiates light having the entire wavelength region of a common visible ray, it is preferred that the excitation filter 111 is installed between the light source unit and the transparent pipe unit so that only the blue-series light of 380 nm to 480 nm of light radiated by the light source unit 150 is transmitted and delivered to the transparent pipe unit.

In contrast, if the light source unit 150 itself radiates only the light having the wavelength of 380 nm to 480 nm, the element of the excitation filter 111 will be excluded.

The detection unit 120 is means for collecting light of the light source unit 150, which is received by the sample moving through the transparent pipeline 50 and reflected by the sample, and detecting an image of the reflected light. The detection unit 120 includes a camera used in an optical microscope.

In this case, it is preferred that a camera capable of monitoring an object of the smallest 10 μm is used as the camera used in the detection unit 120 and the camera has resolution of 1250*1250 pixels or more.

That is, the detection unit 120 is means for detecting an image by focusing light which is reflected by a sample moving through the transparent pipeline 50 and then passes through the optical filter 112. The detection unit 120 is disposed at the location opposite the light source unit 150 in such a way as to receive light emitted by the light source unit 150, focus light reflected by plankton included in the sample, and detect an image of the plankton included in the sample.

That is, if the light source unit 150 radiates light of the entire region of a visible ray, the excitation filter 111 allows only blue-series light belonging to the light radiated by the light source unit and having a wavelength of 380 nm to 480 nm to pass through the transparent pipe unit 150.

Thereafter, the light passing through the excitation filter 111 passes through the optical filter 112 as red-series light of 620 nm to 780 nm, which is radiated by plankton moving through the transparent pipe unit 150. In this case, the optical filter 112 transmits only the red-series light having the wavelength of 620 nm to 780 nm so that it is delivered to the detection unit 120.

In this case, if the light source unit 150 radiates only the blue-series light having the wavelength of 380 nm to 480 nm, only the excitation filter 111 will be excluded.

That is, the energy level of the blue-series light having the wavelength of 380 nm to 480 nm delivered to the transparent pipe unit 150 is converted into that of the red-series light having the wavelength of 620 nm to 780 nm through photosynthesis of chlorophyll included in plankton present within the transparent pipe unit 150, and thus the red-series light having the wavelength of 620 nm to 780 nm is radiated. In this case, the dichroic mirror 112 transmits the radiated red-series light having the wavelength of 620 nm to 780 nm toward the detection unit without any change, thereby generating an image of phytoplankton included in the sample, that is, an object to be examined in the image acquisition unit of the detection unit.

A first light induction member 210 which prevents interference with external light and allowing light radiated by the light source unit 150 to be delivered to the transparent pipe unit 50 without interference may be coupled between the light source unit 150 and the transparent pipe unit 50.

Furthermore, a second light induction member 230 which prevents interference with external light, penetrates the transparent pipe unit 150, and allows light reflected by plankton included in the sample to be focused on the detection unit 120 may be coupled between the transparent pipe unit 150 and the detection unit 120.

In this case, the excitation filter 111 may be installed within the first light induction member 210, and the optical filter 112 may be installed within the second light induction member 230.

In this case, a housing 200 which modulates the light source unit 150, the transparent pipe unit 50, and the first and the second light induction members 210 and 230 may be further included.

The detection unit 120 includes an image acquisition unit 121 which detects light reflected by plankton included in the sample, generates an image of the plankton included in the sample, and displays the generated image on a screen and an image processing unit 122 which analyzes each of pixels included in the screen on which the generated image is displayed, determines the number of plankton included in the sample, determines a plurality of pixels that belongs to the pixels included in the screen and continuously emits light to be a single object, calculates a total number of objects included in the screen, and determines the total number of objects to be a total number of target plankton included in the screen.

That is, the image acquisition unit 121 detects light passed through the optical filter 112, that is, light reflected by plankton included in the sample and generates an image of the plankton included in the sample.

Furthermore, the image processing unit 122 analyzes each of the pixels included in the screen on which the generated image is displayed, determines the number of plankton included in the sample, determines a plurality of pixels that belongs to the pixels included in the screen and continuously emits light to be a single object, calculates a total number of objects included in the screen, and determines the total number of objects to be a total number of target plankton included in the screen.

The image acquisition unit 121 includes the aforementioned camera and is means for detecting light reflected by plankton included in the sample and generating an image of the plankton included in the sample.

It is preferred that a camera capable of monitoring an object of the smallest 10 μm is used as the camera forming the image acquisition unit 121 as described above. It is preferred that the camera has resolution of 1250*1250 pixels or more.

The image processing unit 122 is means for determining the number of plankton included in the sample by analyzing the image generated by the image acquisition unit 121.

In this case, the image processing unit 122 determines the number of plankton included in the sample by analyzing each of the pixels included in the screen on which the generated image is displayed.

That is, an image of plankton is displayed on the screen on which the image is displayed by red-series light reflected by the plankton. The number of displayed images of the plankton is checked.

In this case, the image processing unit 122 determines a plurality of pixels that belongs to the pixels included in the screen and continuously emits light to be a single object, determines each of the determined objects to be a single plankton object, and calculates the number of individuals of plankton included in the sample, that is, the number of individuals of target plankton.

That is, the image processing unit 122 determines a plurality of pixels that belongs to the pixels forming the screen, emits red-series light, and continuously emits light to be a single object forming a single piece of plankton and calculates a total number of target plankton, that is, an object to be examined which is included in the screen.

In this case, it is preferred that the image processing unit 122 performs processing so that the plurality of pixels that is determined to be the single object and that continuously emits light includes only pixels continuously emitting light within a predetermined contrast range along with neighboring pixels. That is, it is preferred that the image processing unit 122 sets the plurality of pixels that is determined to be the single object and that continuously emits light as a plurality of pixels that belongs to the pixels included in the screen and that is continuously present within a predetermined contrast range along with one or more neighboring pixels.

That is, assuming that 5 pixels forming a single object continuously emit light, if 3 of the 5 pixels continuously emit light within the range of a predetermined contrast range and the remaining 2 pixels continuously emit light out of the range of the predetermined contrast range, only the 3 pixels continuously emitting light within the range of the predetermined contrast range is determined to form a single object. In this case, the image processing unit 122 may determine that the corresponding object includes only the 3 pixels.

The image processing unit 122 determines a plurality of pixels that belongs to the pixels included in the screen and continuously emits light to be a single object, calculates a total number of the objects included in the screen, and determines a total number of the target plankton included in the screen, but may determine only objects that belong to the objects and each have the number of a plurality of pixels continuously emitting light within the range of a predetermined number to be target plankton.

That is, only when the number of a plurality of pixels forming the single object is within the range of a predetermined number, the plurality of pixels is determined to be target plankton to be calculated.

This is for excluding floating matters, etc. other than plankton to be actually checked by previously setting the range of the number of continuous pixels corresponding to the size of actually problematic target plankton.

That is, assuming that the number of a plurality of pixels continuously emitting light in the screen was detected to be 10, that is, 10 objects were detected, and the range of the predetermined number of pixels continuously emitting light so that they are determined to be a single piece of target plankton was preset to be 4~6, if 2 pixels continuously emit light in 2 of the 4 objects of the 10 objects, 15 pixels continuously emit light in the remaining 2 of the 4 objects of the 10 objects, and 4 to 6 pixels continuously emit light only in the remaining 6 objects of the 10 objects, only the remaining 6 objects are determined to be target plankton and determined to be a total number of target plankton included in the screen.

Furthermore, it is preferred that the image processing unit 122 excludes an object of the objects determined to be the target plankton from the target plankton if an average brightness or intensity value of light of all of pixels forming a single object is out of a predetermined brightness to intensity range of light.

The reason for this is that a specific range of brightness to intensity of light emitted by actually problematic plankton is previously set and only when an average brightness or intensity value of light of a plurality of pixels forming each of the objects is included in the predetermined specific range of brightness to intensity of light, a corresponding object is determined to be active target plankton that is actually alive and active.

That is, this is for excluding deactivated objects of determined objects and including only actually active objects of the determined objects in the final calculation because deactivated, that is, actually dead plankton that rarely has activity, generates intensity o brightness of weak light.

For example, in the above example, if the intensity range of brightness of light for each of images of plankton that is active as an actual living body is, for example, a range of 10 luces to 20 luces and a range of predetermined brightness is set as 10 luces to 20 luces in the image processing unit, target plankton that belongs to the 6 pieces of target plankton and is out of the range of 10 luces to 20 luces is excluded from actual target plankton.

In this case, a certain range of the predetermined brightness or intensity of light may be set using various existing units for brightness or intensity of light, such as lumen (the speed of light) or lux (luminous intensity), or a candela (cd).

Furthermore, the detection unit digitizes the image of the collected light and represents the image so that it has a value between 0 at which brightness of each of the pixels forming the image has not been actually detected and 256 at which brightness of each of the pixels forming the image has the greatest brightness of light. A certain range of the predetermined brightness or intensity of light may be previously set in a range of a proper value between the values 0 to 256.

Figure 11:
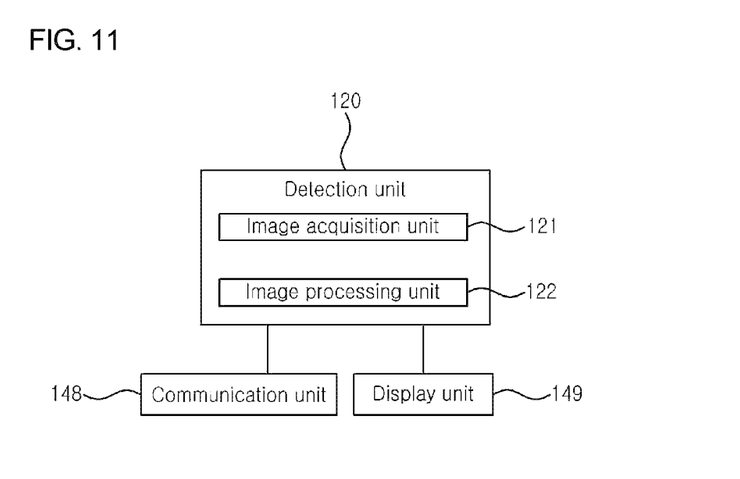
FIG. 11 is a block diagram further illustrating a detection unit.

The plankton examination apparatus according to the present invention may further include a communication unit 148 which is connected to the detection unit 120 and capable of receiving an image of plankton generated by the image acquisition unit 121 and/or information about a total number of target plankton calculated by the image processing unit 122 and transmitting the image and information to a separate examination and check system.

Furthermore, the plankton examination apparatus according to the present invention may further include a display unit 149 connected to the detection unit 120 and for displaying an image of plankton generated by the image acquisition unit 121 and/or information about a total number of target plankton calculated by the image processing unit 122.

Through the aforementioned construction, the present invention provides the plankton examination apparatus directly installed in a pipeline through which ballast water or seawater moves and capable of precisely checking a total number of individuals of problematic plankton included in a sample using ballast water or seawater included in the transparent pipe unit 50 as the sample.

Those skilled in the art to which the present invention pertains will appreciate that the present invention may be implemented in other detailed forms without departing from the technical spirit or essential characteristics of the present invention. Accordingly, the aforementioned embodiments should be understood as being only illustrative, but should not be understood as being restrictive from all aspects. The scope of the present invention is defined by the following claims rather than the detailed description, and the meanings and scope of the claims and all changes or modified forms derived from their equivalents should be construed as falling within the scope of the present invention.

What is claimed is:

1. A plankton examination apparatus, comprising:
a sub-pipe in which a transparent pipe unit comprising a light-transmitting member formed in some section of the sub-pipe and through which a sample comprising plankton moves;
a light source unit which radiates only blue-series light having a wavelength of 380 nm to 480 nm from a direction on one side outside the transparent pipe unit to a direction on an other side of the transparent pipe unit;
a detection unit which receives light radiated in the direction on the other side outside the transparent pipe unit through the transparent pipe unit from the light source unit and generates an image of the plankton included in the sample flowing through the transparent pipe unit; and
a dichroic mirror installed between the transparent pipe unit and the detection unit in such a way as to transmit only red-series light which belongs to the light radiated by the light source unit and passed through the transparent pipe unit and has a wavelength of 620 nm to 780 nm and to deliver the red-series light to the detection unit;
wherein the detection unit comprises:
an image acquisition unit which detects light reflected by the plankton included in the sample, generates the image of the plankton included in the sample, and displays the generated image on a screen; and
an image processing unit which analyzes each of pixels included in the screen on which the generated image is displayed and determines a number of the plankton included in the sample, wherein the image processing unit determines a plurality of pixels belonging to the pixels included in the screen and continuously emitting light to be a single object, calculates a total number of objects included in the screen, and determines the total number of objects to be a total number of target plankton included in the screen, wherein the image processing unit excludes an object of the objects determined to be the target plankton from the target plankton if an average brightness or intensity value of light of all of pixels forming the object is out of a predetermined brightness or intensity range of light, that is, a brightness or intensity range of light emitted by alive target planktons.

2. A plankton examination apparatus, comprising:
a sub-pipe in which a transparent pipe unit comprising a light-transmitting member formed in some section of the sub-pipe and through which a sample comprising plankton moves;
a light source unit which radiates light from a direction on one side outside the transparent pipe unit to a direction on an other side of the transparent pipe unit;
a detection unit which receives light radiated in the direction on the other side outside the transparent pipe unit through the transparent pipe unit from the light source unit and generates an image of the plankton included in the sample flowing through the transparent pipe unit;
an excitation filter installed between the light source unit and the transparent pipe unit in such a way as to transmit only blue-series light belonging to the light radiated by the light source unit and having a wavelength of 380 nm to 480 nm and to deliver the blue-series light to the transparent pipe unit; and
a dichroic mirror installed between the transparent pipe unit and the detection unit in such a way as to transmit only red-series light which belongs to the light radiated by the light source unit and passed through the transparent pipe unit through the excitation filter and has a wavelength of 620 nm to 780 nm and to deliver the red-series light to the detection unit;
wherein the detection unit comprises:
an image acquisition unit which detects light reflected by the plankton included in the sample, generates the image of the plankton included in the sample, and displays the generated image on a screen; and
an image processing unit which analyzes each of pixels included in the screen on which the generated image is displayed and determines a number of the plankton included in the sample, wherein the image processing unit determines a plurality of pixels belonging to the pixels included in the screen and continuously emitting light to be a single object, calculates a total number of objects included in the screen, and determines the total number of objects to be a total number of target plankton included in the screen, wherein the image processing unit excludes an object of the objects determined to be the target plankton from the target plankton if an average brightness or intensity value of light of all of pixels forming the object is out of a predetermined brightness or intensity range of light, that is, a brightness or intensity range of light emitted by alive target planktons.

3. The plankton examination apparatus of claim 1, wherein:
a first light induction member which prevents interference with external light and allows the light radiated by the light source unit to be delivered to the transparent pipe unit through the excitation filter without interference is coupled between the light source unit and the transparent pipe unit, and
a second light induction member which prevents interference with external light, penetrates the transparent pipe unit, and allows light reflected by the plankton included in the sample to be focused on the detection unit is coupled between the transparent pipe unit and the detection unit.

4. The plankton examination apparatus of claim 1, wherein the image processing unit determines only a corresponding object belonging to the objects and having a number of a plurality of pixels continuously emitting light within a range of a predetermined number to be the target plankton and determines the total number of target plankton included in the screen by calculates the total number of target plankton included in the screen.

5. The plankton examination apparatus of claim 2, wherein:
a first light induction member which prevents interference with external light and allows the light radiated by the light source unit to be delivered to the transparent pipe unit through the excitation filter without interference is coupled between the light source unit and the transparent pipe unit, and a second light induction member which prevents interference with external light, penetrates the transparent pipe unit, and allows light reflected by the plankton included in the sample to be focused on the detection unit is coupled between the transparent pipe unit and the detection unit.

6. The plankton examination apparatus of claim 2, wherein the image processing unit determines only a corresponding object belonging to the objects and having a number of a plurality of pixels continuously emitting light within a range of a predetermined number to be the target plankton and determines the total number of target plankton included in the screen by calculates the total number of target plankton included in the screen.

* * * * *